(12) United States Patent
Callaghan et al.

(10) Patent No.: US 7,387,807 B2
(45) Date of Patent: Jun. 17, 2008

(54) TOPICAL COMPOSITION COMPRISING FEVERFEW

(75) Inventors: Theresa Callaghan, Delft (NL); Thierry Oddos, Meudon (FR); Gerard Gendimenico, Neshanic Station, NJ (US); Katharine Martin, Ringoes, NJ (US)

(73) Assignee: Johnson & Johnson Consumer France, SAS, Roc Division (FR)

( * ) Notice: Subject to any disclaimer, the term of this patent is extended or adjusted under 35 U.S.C. 154(b) by 636 days.

(21) Appl. No.: 11/154,606

(22) Filed: Jun. 16, 2005

(65) Prior Publication Data

US 2005/0244525 A1 Nov. 3, 2005

Related U.S. Application Data

(60) Continuation of application No. 10/721,537, filed on Nov. 25, 2003, now Pat. No. 7,229,650, which is a division of application No. 10/139,498, filed on May 6, 2002, now abandoned, which is a division of application No. 09/586,587, filed on Jun. 2, 2000, now Pat. No. 6,410,062.

(60) Provisional application No. 60/137,332, filed on Jun. 3, 1999.

(51) Int. Cl.
*A61K 36/28* (2006.01)
(52) U.S. Cl. .......................... 424/764; 424/401; 424/729
(58) Field of Classification Search ........................ None
See application file for complete search history.

(56) References Cited

U.S. PATENT DOCUMENTS

| | | | |
|---|---|---|---|
| 3,755,560 A | 8/1973 | Dickert et al. |
| 4,254,105 A | 3/1981 | Fukuda |
| 4,421,769 A | 12/1983 | Dixon et al. |
| 4,758,433 A | 7/1988 | Johnson et al. |
| 4,960,764 A | 10/1990 | Figueroa, Jr. et al. |
| 5,260,065 A | 11/1993 | Mathur et al. |
| 5,384,121 A | 1/1995 | Rhodes |
| 5,905,089 A | 5/1999 | Hwang et al. |
| 6,103,218 A | 8/2000 | Burcker et al. |
| 6,130,254 A | 10/2000 | Fisher et al. |
| 6,153,208 A | 11/2000 | McAtee et al. |
| 6,224,875 B1 | 5/2001 | Bombardelli et al. |
| 6,410,062 B1 | 6/2002 | Callaghan et al. |
| 6,479,080 B2 | 11/2002 | Bombardelli et al. |
| 6,620,419 B1 | 9/2003 | Lintner |
| 2001/0021400 A1 | 9/2001 | Bombardelli et al. |
| 2002/0182166 A1 | 12/2002 | Martin et al. |
| 2003/0003170 A1 | 1/2003 | Callaghan et al. |
| 2003/0077343 A1 | 4/2003 | Martin et al. |

FOREIGN PATENT DOCUMENTS

EP 0 427 411 B1 5/1991
EP 0 273 202 B1 6/1995
WO WO9406800 3/1994
WO WO 96/31194 A2 10/1996
WO WO 97/02807 A1 1/1997
WO WO00/74695 A2 12/2000
WO WO00/74699 A1 12/2000
WO WO02/074280 A1 9/2002

OTHER PUBLICATIONS

Johnson, Timothy, CRC Ethnobotany Desk Reference, CRC Press, NY, 1999, pp. 198-199,516-517,823-824.
International Plant Names Index published on the Internet, http://www.ipni.org, May 2003.
Connor, Michael, Wheeler, Larry, Depletion of Cutaneous Glutathione by Ultraviolet Radiation, Photochemistry and Photobiolgy, 1987,vol. 46, No. 2, pp. 239-245.
Fisher, Gary J., Voorhees, John J., Molecular Mechanisms of Photoaging and its Preventions by Retinoic Acid: Ultraviolet Irradiation Induces MAP Kinase Signal Transduction Cascades that Induce AP-1-Regulated Matrix Metalloproteinases that Degrade Human Skin In Vivo, The Society for Investgative Dermatology, Inc. 1998pp. 61-68.
Fisher, Gary J., Subhash C. Datta, Harvinder S. Talwar, Zeng-Quan Wang, James Varani, Sewon Kang and Voorhees, John J., Nature, 1996, vol. 379, pp. 335-339.
Meister, Alton, Glutathione, Ascorbate, and Cellular Protection, Cancer Research Suppl, 54,1994,pp. 1969s-1975s.
Mezei, Michael, Liposomes as a Skin Drug Delivery System, Elsevier Science Publishers , NY,1985,pp. 345-358.
Mezei, Michael, Gulasekharam, Vijeyalakshmi, Liposomes-A Selective Drug Delivery System for the Topical Route of Administration: Gel Dosage Form, J. Pharm. Pharmacol, 1982,34:473-474.
Steenvoorden, David, Hasselbaink, Danny, Beijersbergen Van Henegouwen, Gerard M.J., Protection Against UV-Induced Reactive Intermediates In Human Cells And Mouse Skin By Glutathione Precursors: A Comparison Of N-Acetylcystein And Glutathione Ethylester, Photochemistry and Photobiology, 1998,67(6):pp. 651-656.
Tyrrell, R.M., Pidoux, M., Correlation Between Endogenous Glutathione Content and Sensitivity of Cultured Human Skin Cells to Radiation at Defined Wavelengths in the Solar Ultraviolet Range, Photochemistry and Photobiology, 1998, vol. 47, No. 3, ppd. 405-412.

(Continued)

*Primary Examiner*—Susan Coe Hoffman

(57) ABSTRACT

This invention relates to a method of treating and preventing inflammatory disorders and related conditions using an extract of feverfew. Particularly, the invention includes a method of treating and preventing inflammatory disorders and related conditions which comprises applying a topical composition comprising an effective amount of an extract of feverfew to a patient and a method of treating and preventing inflammatory disorders and related conditions of the skin by applying a topical composition containing an effective amount of an extract of feverfew to a patient. In addition, the invention includes a method of treating and preventing inflammatory disorders and related conditions by applying a topical composition containing an effective amount of an extract of feverfew to a patient where said extract is substantially free of $\alpha$-unsaturated $\gamma$-lactone.

26 Claims, 1 Drawing Sheet

OTHER PUBLICATIONS

Van Den Broeke, Leon T., Beijersbergen Van Henegouwen, Gerard, M. J., Topically applied N-acetylcysteine as a protector against UVB-induced systemic immunosuppression, Journal of Photochemistry and Photobiology, B: Biology 27, 1995:pp. 61-65.

Sagarin, Edward and Balsam, M.S., Cosmetics Science and Technology, Second Edition, vol. 1, (1972) pp. 32-43.

Wenningen, John A., McEwen, G.N. Jr., International Cosmetic Ingredient Dictionary and Handbook, Seventh Edition (1997)vol. 2, The Cosmetic, Toiletry, and Fragrance Association, Washington, DC, pp. 1626,1650-1667, 1654-1661, 1693-1697, 1673-1686.

Titheradge, Michaela., The Enzymatic Measurement of Nitrate and Nitrite, Methods in Molecular Biology, vol. 100, publicly available prior to Mar. 1, 2002, pp. 83-91.

Detmar, Michael, The Role of VEGF and thrombospondins in skin agiogenesis, Journal of Dermatological Science, 24 Suppl, 1 (2000)S78-S84.

Kollias, N., Baqer, A. Sadiq, i. Sayre, R.M., In vitro and in vivo Ultraviolet-Induced Alterations of Oxy-and Deoxyhemoglobin, Photochemistry and Photobiology vol. 56, No. 2, (1991) pp. 223-227.

Guy, R.H. and Maibach, H.I., Rapid Radial Transport of Methyl Nicotinate in the Dermis, Arch Dermatol Res (1982)273:91-95.

Yancopoulos, George D., Davis, Samuel, Gale, Nicholas W., Rudge, John S., Wiegand Stanley J., Holash, Jocelyn, Vascular-specific growth factors and blood vessel formation, Nature, vol. 407, (2000)pp. 242-248.

Bikfalvi, Andreas, Klein, Sharon, Pintucci, Giuseppe, Rifkin, Daniel B., Biological Roles of Fibroblast Growth Factor-2, Endocrine Reviews, vol. 18, No. 1, pp. 26-45.

Gerber, Hans-Peter, McMurtrey, Amy, Kowalski, Joe, Yan, Minhong, Keyt, Bruce A, Dixit, Vishva, Ferara, Napoleone, Vascular Endothelial Growth Factor Regulates Endothelial Cell Survival through the Phosphatidylinositol 3'-Kinase/Akt Signal Transduction Pathway, The Journal of Biological Chemistry, (1998), vol. 273,No. 46, pp. 30336-30343.

McCutcheon's Emulsifiers & Detergents, 1986 (North Edition), McPublishing Co., Glen Rock, NJ, pp. 317-324.

Barel, A.O., Courage, W. Clarys, P. , Suction Method for Measurement of Skin Mechanical Properties:The Cutometer®, Handbook of Non-Invasive Methods and the Skin, eds. J. Serup & G. Jemec, Chapter 14.3(1995) pp. 335-340.

Abstract, Acta Derm Venereol 1983:63(4):308-14, Contact allergy to parthenolide in Tanacetum parthenium (L.) Schulz-Bip. (feverfew, Asteraceae)and cross-reactions to related sesquiterpene lactone containing Compositae species.

Derwent English abstract of Hu 210294 B (1995).

Contact Dermatitis 1988, 38(4):207-8.

Lamminpaa et al. Contact Dermatitis (1996), vol. 34, No. 5, pp. 330-335.

Arch. Dermatol. Forsch 1975, 251(3):235-44.

Arch. Dermatol. Res. 1976, 255(2):111-21.

Barasby et al. Planta Medica (1993) vol. 59, No. 1, pp. 20-25.

Am. J. Contact Dermatol. 1998-9(1):49-50.

Br. J. Dermatol. 1995, 132(4):543-47.

XP-002147441 Biosis: Biosciences Information Service, Barqasby R.S.J. et al.: Philadelphia, PA 1993.

Hanada, K. et al. "Photoprotective Effect of Esterified Glutathione Against Ultraviolett B-Induced Sunburn Cell formation in the Hairless Mice". The Society for Investigative Dermatology, Inc., 1997, pp. 727-730.

Hausen, B.M. et al. "Chrysanthemum Allergy, Identification of Allergens". Archives for Dermatological Research, 255, pp. 111-121 (1976).

Menage, H. et al. "Contact and Photocontact Sensitization in Chronic Actinic Dermatitis: Sesquiterpene Lactone Mix is an Important Allergen", British Journal of Dermatology, 1995, 132: pp. 543-547.

Orion, E. et al. "Comparison of Simultaneous Patch Testing with Parthenolide and Sesquiterpene Lactone Mix", Contact Dermatitis, 1998, 38, pp. 207-208.

Spettoli, E. et al. "Contact Dermatitis Caused by Sesquiterpene Lactones", American Journal of Contact Dermatitis, vol. 9, No. 1, Mar. 1998, pp. 49-60.

Schulz, K. et al. "Chrysanthemem-Allergie", Archives Derm. Forsch. 251, pp. 235-244 (1975).

TOPICAL COMPOSITION COMPRISING FEVERFEW

CROSS REFERENCE TO RELATED APPLICATIONS

This patent application is a continuation patent application of U.S. Ser. No. 10/721,537, filed Nov. 25, 2003, now U.S. Pat. No. 7,229,650, which is a divisional application of U.S. Ser. No. 10/139,498, filed May 6, 2002, now abandoned, which is a divisional application of U.S. Ser. No. 09/586,587, filed June 2, 2000, now patent application Ser. No. 6,410, 062B1, which claims priority from provisional application U.S. Ser. No. 60/137,332, filed Jun. 3, 1999, and is incorporated herein by reference.

FIELD OF THE INVENTION

This invention relates to the topical treatment and prevention of inflammatory disorders and related conditions using extracts of feverfew (*Tanacetum parthenium*).

BACKGROUND OF THE INVENTION

*Tanacetum parthenium*, a plant commonly known as Feverfew, has been recognized since the Middle Ages as having significant medicinal properties when taken orally—used as a general febrifuge, hence its common name. Many have isolated extracts of the plant and those extracts have been used to orally treat miigraines, arthritis, and bronchial complaints. (See Johnson et al, U.S. Pat. No. 4,758,433, discussing the treatment of a variety of diseases by oral, inhalation, injection or suppository administration of the extract and see WO 94 06800, discussing a extract of feverfew which contains parthenolide).

Extracts of feverfew contain many components. Although not all components have been isolated and characterized, the known components of an extract of feverfew contain a significant number of biologically active components. To date, the chemical constituents of whole feverfew extract are as follows: apigenin-7-glucoside, apigenin-7-glucuronide, 1-β-hydroxyarbusculin, 6-hydroxykaempferol-3,7-4'-trimethylether (Tanetin), 6-hydroxykaempferol-3,7-dimethyl ether, 8-β-reynosin, 10-epicanin, ascorbic acid, beta-carotene, calcium, chromium, chrysanthemolide, chrysanthemomin, chrysarten-A, chrsyarten-c, chrysoeriol-7-glucuronide, cobalt, cosmosiin, epoxyartemorin, luteolin-7-glucoside, luteolin-7-glucuronide, mangnoliolide, parthenolide, quercetagentin-3,7,3'-trimethylether, quercetagetin-3'7-dimethylether, reynosin, tanaparthin, tanaparthin-1α,4α-epoxide, tanaparthin-1β,4β-epoxide, β-costunolide, 3-β-hydroxy-parthenolide, and 3,7,3'-trimethoxyquercetagetin. The specific role that each of these component compounds plays in the biological activity of feverfew is to date unknown. However, some information is known about the alergic reactions to the extract. It is believed that many of these allergic reactions are caused by the α-unsaturated γ-lactones such as parthenolide. (See, Arch. Dermatol. Forsch. 1975, 251 (3):235-44; Arch. Dermatol. Forsch 1976, 255 (2):111-21; Contact Dermatitis, 1988, 38 (4):207-8; Am. J. Contact Dermatol. 1998-9 (1):49-50; Br. J. Dermatol, 1995, 132 (4): 54347).

Despite the existence of oral methods of using extracts of feverfew, there are no defined methods for topically using these extracts to treat or prevent inflammatory disorders and related conditions. In addition, there are no teachings which describe the use of an extract of feverfew which does not contain the allergy causing α-unsaturated γ-lactones. These are two areas which are addressed by this invention.

SUMMARY OF THE INVENTION

This invention relates to a method of treating or preventing inflammatory disorders and related conditions using an extract of feverfew. More particularly, the invention includes a method of treating or preventing inflammatory disorders and related conditions by applying a topical composition containing an effective amount of an extract of feverfew to a patient. The method of this invention includes a method of treating or preventing inflammatory disorders and related conditions of the skin by applying a topical composition comprising an effective amount of an extract of feverfew to a patient. Still further, the invention includes a method of treating and preventing inflammatory disorders and related conditions by applying a topical composition containing an effective amount of an extract of feverfew to a patient where said extract is substantially free of α-unsaturated γ-lactone. Further, the invention includes a method of treating and preventing inflammatory disorders and related conditions of the skin by applying a topical composition containing an effective amount of an extract of feverfew to a patient where said extract is substantially free of α-unsaturated γ-lactone.

DETAILED DESCRIPTION OF THE INVENTION

Figure 1:
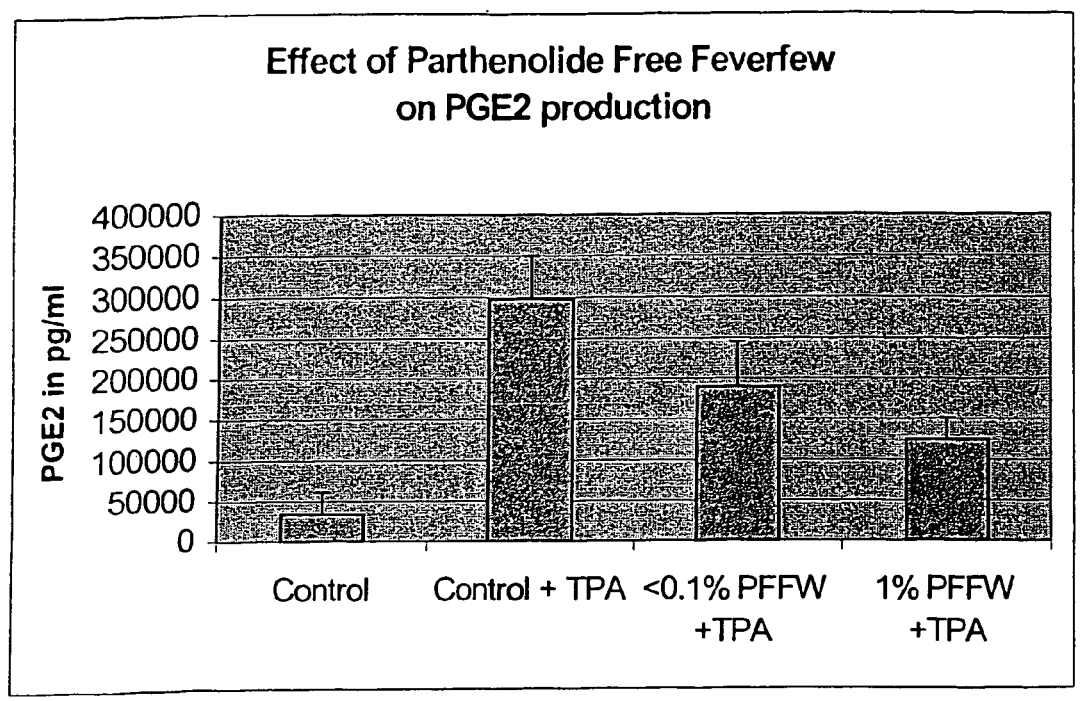
FIG. 1 shows the effect of parthenolide-free feverfew on PGE-2 production.

This invention includes a method of treating and preventing inflammatory disorders and related conditions by applying a topical composition containing an effective amount of an extract of feverfew to a patient.

Inflammatory disorders and relate conditions which may be treated or prevented by topical use of the compositions of this invention include, but are not limited to the following: arthritis, bronchitis, contact dermatitis, atophic dermatitis, psoriasis, seborrheic dermatitis, eczema, allergic dermatitis, polymorphous light eruptions, inflammatory dermatoses, folliculitis, alopecia, poison ivy, insect bites, acne inflammation, irritation induced by extrinsic factors including, but not limited to, chemicals, trauma, pollutants (such as cigarette smoke) and sun exposure, secondary conditions resulting from inflammation including but not limited to xerosis, hyperkeratosis, pruritus, post-inflammatory hyperpigmentation, scarring and the like. Preferably, the inflammatory disorders and related conditions which may be treated or prevented using the methods of the invention are arthritis, inflammatory dermatoses, contact dermatitis, allergic dermatitis, atopic dermatitis, polymorphous light eruptions, irritation, including erythema induced by extrinsic factors, acne inflammation, psoriasis, seborrheic dermatitis, eczema, poison ivy, insect bites, folliculitis, alopecia, and secondary conditions and the like.

"Feverfew" is a plant belonging to the family of Asteraceae/Composite which is technically known as, *Tanacetum parthenium, Altamisa, Crisanthemum, Leucanthemum*, or *Pyrethrum parthenium*.

The term "effective amount" refers to the percentage by weight of the feverfew extract in the topical composition which is needed to treat an inflammatory disorder or related condition in a patient. Preferably the effective amount is between about 0.0005 to about 20% by weight of the composition. More preferably, the concentration should be less than about 10% by weight of the topical composition. Even more preferably between about 0.001% and about 10%, and most preferably between about 0.01% and about 2%.

The term "patient" refers to a mammal which is being treated prophylactically for an inflammatory condition and/or for an inflammatory condition with visible symptoms. Preferably the patient is a human.

Further, the invention includes a method of treating and preventing inflammatory disorders and related conditions of the skin by applying a topical composition containing an effective amount of an extract of feverfew to a patient.

The terms, inflammatory disorder and related condition, feverfew, effective amount, and patient, have their aforementioned meanings. The term "skin" includes all surfaces of a patient, such as the exposed hide or surfaces covered by hair.

The invention also includes a method of treating and preventing inflammatory disorders and related conditions which comprises applying a topical composition comprising an effective amount of an extract of feverfew to a patient where said extract is α-unsaturated γ-lactone-deprived.

The terms, inflammatory disorders and related conditions, feverfew, effective amount, and patient have their aforementioned meanings. The term "substantially free of α-unsaturated γ-lactone", refers to an extract of feverfew having a weight content of the α-unsaturated γ-lactones found in natural feverfew extracts of less than about 0.2% by weight. These α-unsaturated γ-lactones include but are not limited to parthenolide ([1αR-(1a R*, 4E,7a S*,10a S*,10b R*)]2,3,4,7,7a,8,10a,10b-octahydro-1a,5-dimethyl-8-4,5α-epoxy-6β-hydroxy-germacra-1(10),11(13)-dien-12-oic acid γ-lactone), 3-β-hydroxy-parthenolide, costunolide, 3-β-constunolide, artemorin, 8α-hydroxy-estafiatin, chysanthemolide, magnoliolide, tanaparthin, tanaparthin-1α,4α-epoxide, tanaparthin-1β,4β-epoxide, chrysanthemonin, and other sesquiterpenes. Preferably, the feverfew extract has a weight content of α-unsaturated γ-lactone below about 0.2. Preferably the α-unsaturated γ-lactone is parthenolide. The method of preparing this parthenolide-deprived extract is described in an Italian patent application (MI99A001244, filed on Jun. 3, 1999) which is hereby incorporated by reference. Since the α-unsaturated γ-lactones cause some of the allergic reactions to extracts of feverfew, topical compositions made from α-unsaturated γ-lactone-deprived extracts are expected to be non-irritating.

This invention also includes a method of treating inflammatory disorders and related conditions of the skin by applying a topical composition comprising an effective amount of an extract of feverfew to a patient where said extract is substantially free of α-unsaturated γ-lactone.

The terms inflammatory disorders and related conditions, feverfew, effective amount, paiie-nt, skin-, and α-unsaturated γ-lactone-deprived have their aforementioned meanings.

In addition to the extracts of feverfew, other substances, such as biologically active agents, pharmaceutical excipients, and cosmetic agents may be included in the topical compositions of this invention.

Biologically active agents may include, but are not limited to, flavanoid/flavone compounds which include but are not limited to tanetin, 3,7,3'-trimethoxyquercetagetin, apigenin and its derivatives. When flavanoid/flavone compounds are present, they are present at a concentration of between about 0.001% to about 0.5% preferably, between about 0.005% and 0.2% based on the weight of the topical composition.

Additional biologically active agents include but are not limited to sunscreens, anti-wrinkling/antiaging agents, antifungal agents, antibiotic agents, anti-acne and antipsoriatic agents, depigmentating agents, where such agents may be utilized so long as they are physically and chemically compatible with the other components of the topical composition.

The compositions of this invention may include additional skin actives. Actives can be but not limited to vitamin compounds. Skin lightening agents (kojic acid, ascorbic acid and derivatives such as ascorbyl pamiltate, and the like); antioxidant agents such as tocopherol and esters; metal chelators, retinoids and derivatives, moisturizing agents, hydroxy acids such as salicylic acid, sun screen such as octyl methoxycinnamate, oxybenzone, avobenzone, and the like, sun blocks such as titanium oxide and zinc oxide, and skin protectants. Mixtures of above skin actives may be used.

Sunscreens which may be used in the compositions of this invention may include but are not limited to organic or inorganic sunscreens, such as, octylmethoxycinnamate and other cinnamate compounds, titanium dioxide, zinc oxide and the like.

Anti-wrinkling/anti-aging agents may include but are not limited to retinoids (for example, retinoic acid, retinol, retinal, retinyl acetate, and retinyl palmitate) alpha hydroxy acids, galactose sugars (for example, melibiose and lactose), antioxidants, including but not limited to water soluble antioxidants such as sulfhydryl compounds and their derivatives (for example, sodium metabisulfite and N-acetyl-cysteine, acetyl-cysteine), lipoic acid and dihydrolipoic acid, resveratrol, lactoferin, ascorbic acid and ascorbic acid derivatives (for example ascorbyl palmitate and ascorbyl polypeptide). Oil soluble antioxidants suitable for use in the compositions of this invention include, but are not limited to tocopherols (for example, tocopheryl acetate, α-tocopherol), tocotrienols and ubiquinone. Natural extracts containing antioxidants suitable for use in the compositions of this invention, include, but not limited to extracts containing flavonoids, phenolic compounds, flavones, flavanones, isoflavonoids, mono, di- and tri-terpenes, sterols and their derivatives. Examples of such natural extracts include grape seed, green tea, pine bark and propolis extracts and legume extracts and the like.

Antifungal agents include but are not limited to miconazole, econazole, ketoconazole, itraconazole, fluconazole, bifoconazole, terconazole, butoconazole, tioconazole, oxiconazole, sulconazole, saperconazole, clotrimazole, undecylenic acid, haloprogin, butenafine, tolnaftate, nystatin, ciclopirox olamine, terbinafine, amorolfine, naftifine, elubiol, griseofulvin, and their pharmaceutically acceptable salts.

Antibiotic (or antiseptic agents) include but are not limited to but are not limited to mupirocin, neomycin sulfate, bacitracin, polymyxin B, 1-ofloxacin, tetracyclines (chlortetracycline hydrochloride, oxytetracycline hydrochloride and tetrachcycline hydrochoride), clindamycin phosphate, gentamicin sulfate, benzalkonium chloride, benzethonium chloride, hexylresorcinol, methylbenzethonium chloride, phenol, quaternary ammonium compounds, triclocarbon, triclosan, tea tree oil, benzoyl peroxide and their pharmaceutically acceptable salts.

Acne ingredients include but are not limited to agents that normalize epidermal differentiation (e.g. retinoids), keratolytic agents (e.g. salicylic acid and alpha hydroxy acids), benzoyl peroxide, antibiotics and compounds or plant extracts that regulate sebum.

Antipsoriatic agents include but are not limited to corticosteroids (e.g., betamethasone dipropionate, betamethasone valerate, clobetasol propionate, diflrasone diacetate, halobetasol propionate, amcinonide, desoximetasone, fluocinonide, fluocinolone acetonide, halcinonide, triamcinolone acetate, hydrocortisone, hydrocortisone valerate, hydrocortisone butyrate, aclometasone dipropionte, flurandrenolide, mometasone furoate, methylprednisolone acetate), Vitamin D and its analogues (e.g. calcipotriene), retinoids (e.g. Tazarotene) and anthraline.

Cosmetic agents which may be used in the compositions of this invention may include, but are not limited to those agents which prevent potential skin irritation, such as emollients, vitamins and antioxidants (e.g., vitamin E) and herbal extracts (e.g., aloe vera). Further, the cosmetic agents may include humectants, antioxidants/preservatives, plant extracts, flavors, fragrances, surface active agents, and the like. Examples of humectants include glycerol, sorbitol, propylene glycol, ethylene glycol, 1,3-butylene glycol, polypropylene glycol, xylitol, maltitol, lactitol, oat protein, allantoin, acetamine MEA, hyaluronic acid and the like. They may be used either singly or in combination.

Cosmetic agents may also include substances which mask the symptoms of inflammatory disorders and related conditions; such substances include but are not limited to pigments, dyes, and other additives (e.g., silica, talk, zinc oxide, titanium oxide, clay powders). The pharmaceutical excipients include but are not limited to pH modifying agents such as pH-modifying agents, organic solvents (e.g., propylene glycol, glycerol, etc.), cetyl alcohol, kaolin, talc, zinc oxide, titanium oxide, cornstarch, sodium gluconate, oils (e.g., mineral oil), ceteareth-20, ceteth-2, surfactants and emulsifiers, thickener (or binders), perfume, antioxidants, preservatives, and water.

Binders or thickeners may be used in the compositions of this invention to provide substantivity and physical stability to the compositions. Binders or thickeners suitable for use in the compositions of this invention include cellulose derivatives such as alkali metal salts of carboxymethylcellulose, methyl cellulose, hydroxyethyl cellulose and sodium carboxymethylhydroxyethyl cellulose, alkali metal alginates such as sodium alginate, propylene glycol alginate, gums such as carrageenan, xanthan gum, tragacanth gum, caraya gum and gum arabic, and synthetic binders such as polyvinyl alcohol, polysodium acrylate and polyvinyl pyrrolidone. Thickeners such as natural gums and synthetic polymers, as well as coloring agents and fragrances also are commonly included in such compositions.

Examples of preservatives which may be used in the compositions of this invention include, but are not limited to, salicylic acids chlorhexidine hydrochloride, phenoxyethanol, sodium benzoate, methyl para-hydroxybenzoate, ethyl para-hydroxybenzoate, propyl para-hydroxybenzoate, butyl para-hydroxybenzoate and the like.

Examples of flavors and fragrances which may be used in the compositions of this invention include menthol, anethole, carvone, eugenol, limonene, ocimene, n-decylalcohol, citronellol, a-terpineol, methyl salicylate, methyl acetate, citronellyl acetate, cineole, linalool, ethyl linalool, vanillin, thymol, spearmint oil, peppermint oil, lemon oil, orange oil, sage oil, rosemary oil, cinnamon oil, pimento oil, cinnamon leaf oil, perilla oil, wintergreen oil, clove oil, eucalyptus oil and the like.

The compositions of the present invention may be prepared in a number of forms for topical application to a patient. For example, the composition may be applied in a gel, cream, ointment, shampoo, scalp conditioners, liquid, spray liquid, paint-/brush-on preparation, aerosol, powder or adhesive bandage. In addition the composition may be impregnated on a bandages, hydrocolloid dressing, treatment patch or on cloth wipe products, such as baby wipes or facial wipes.

The compositions of this invention may be in the form of emulsions, such as creams, lotions and the like. Such compositions may have more than one phase and may include surface active agents which enable multiphase emulsions to be manufactured.

Examples of surface active agents which may be used in the compositions of this invention include sodium alkyl sufates, e.g., sodium lauryl sulfate and sodium myristyl sulfate, sodium N-acyl sarcosinates, e.g., sodium N-lauroyl sarcosinate and sodium N-myristoyl sarcosinate, sodium dodecylbenzenesulfonate, sodium hydrogenated coconut fatty acid monoglyceride sulfate, sodium lauryl sulfoacetate and N-acyl glutamates, e.g., N-palmitoyl glutamate, N-methylacyltaurin sodium salt, N-methylacylalanine sodium salt, sodium a-olefin sulfonate and sodium dioctylsulfosuccinate; N-alkylaminoglycerols, e.g., N-lauryldiaminoethylglyecerol and N-myristyldiaminoethylglycerol,N-alkyl-N-carboxymethylammonium betaine and sodium 2-alkyl-1-hydroxyethylimidazoline betaine; polyoxyethylenealkyl ether, polyoxyethylenealkylaryl ether, polyoxyethylenelanolin alcohol, polyoxyethyleneglyceryl monoaliphatic acid ester, polyoxyethylenesorbitol aliphatic acid ester, polyoxyethylene aliphatic acid ester, higher aliphatic acid glycerol ester, sorbitan aliphatic acid ester, Pluronic type surface active agent, and polyoxyethylenesorbitan aliphatic acid esters such as polyoxyethylenesorbitan monooleate and polyoxyethylenesorbitan monolaurate. Emulsifier-type surfactants know to those of skill in the art should be used in the compositions of this invention.

Another important ingredient of the present invention is a dermatologically acceptable carrier. Such a suitable carrier is adequate for topical use. It is not only compatible with the active ingredients described herein, but will not introduce any toxicity and safety issues. An effective and safe carrier varies from about 50% to about 99% by weight of the compositions of this invention, more preferably froma bouat 75% to about 99% of the compositions and most preferably from about 85% to about 95% by weight of the compositions.

The choice of which pharmaceutical excipient or biological agent, or cosmetic agent to use is often controlled or affected by the type of inflammatory disorder or related condition which is being treated. For example, if the compositions of this invention were used to treat a skin inflammation associated with athlete's foot, jock itch or diaper rash, talc would be a preferred pharmaceutical excipient and an anti-fungal agents would be preferred biological agents. If the compositions of this invention were to be used to treat eczema of the scalp, emulsifiers and oils would be preferred pharmaceutical excipients.

The condition of contact dermatitis may be treated by applying a topical composition comprising a feverfew extract where said extract has 1% of feverfew which is substantially free of parthenolides, i.e., the parthenolide concentration of said extract is <0.1%. Due to the extremely low concentration of parthenolide in such a feverfew extract, atopic composition made from this extract will be non-irritating.

The following examples are illustrate, but do not serve to limit the scope of the invention described herein. They are meant only to suggest a method of practicing the invention. Those knowledgeable in the treatment and prevention of inflammatory disorders and related conditions as well as other specialties may find other methods of practicing the invention. However, those methods are deemed to be within the scope of this invention.

EXAMPLE 1

Preparation of Feverfew which is Substantially Free of Parthenolide

Two kilograms of Tanacetum parthenium are extracted at 50-60° C. with 20 L of 70% aqueous methanol. The extract is concentrated under vacuum to about 1 L and diluted with an equal volume of methanol. The resulting solution is extracted with 3×2 liters of n-hexane. The hexane extract is evaporated to dryness under vacuum to yield about 30 g of residue (extract H). The water-methanolic solution is then extracted with 2×0.5 L of methylene chloride. The organic phase are evaporated to dryness under vacuum to yield about 70 g of residues (extract DCM). The water-methanolic phase (extract HM) is set aside. The DCM extract is dissolved in 0.6 L of 90% methanol and treated under stirring with 0.6 L of strong basic resin (Relite 2A) for three-four hours. The suspension is filtered under vacuum and the resin is washed with about 2 L of 90% methanol. The methanolic solution, containing parthenolide and its congeners, is removed. The basic resin is then treated under stirring for one hour with 0.6 L of methanol containing 65 mL of concentrated hydrochloric acid. The resin is filtered under vacuum and washed with a further 2.5 L of methanol. The filtrate and the washings are combined, concentrated under vacuum to about 200 mL and extracted with 3×200 mL of ethyl acetate. The resulting extract (E.A.), containing the flavone components tanetin and congeners, is evaporated to dryness under vacuum, to obtain about 4 g of residue. The residues of the extracts H and E.A. are combined with the extract HM. The resulting solution is evaporated to dryness under vacuum and the solid residue is dried under vacuum at 50° C. to constant weight. About 490 g of extract of departhenolidized *T. parthenium* are obtained which shows, by HPLC analysis, (column Zorbax SB C18; eluent $H_2O$+ 0.01% TFA; B:MeCN+0.01% TFA; gradient A:B:90%-10%: 10%-90%; flow 1 ml/min), a parthenolide content below 0.07%.

EXAMPLE 2

Immunomodulation of Periperal Blood Leukocytes

The ability of feverfew and of parthenolide deprived feverfew to affect the inflammatory responses was illustrated by its ability to reduce the production of lymphocyte function in the following assay. The feverfew ("FFW") used in this experiment was commercially obtained from Indena S.p.A. The parthenolide free feverfew ("PFFW") was obtained by using the method of Example 1.

Human leukocytes were collected from a healthy adult male via leukophoresis, and adjusted to a density of $1\times10^6$ cells/mL in serum free lymphocyte growth medium (LGM-2, Clonetics Corporation, San Diego, Calif.). PBLs were stimulated with 10 μg/mL PHA in the presence or absence of test sample. Following a 48 hour incubation at 37° C. with 5% $CO_2$, supernatant was removed and evaluated for cytokine content using commercially available colorimetric ELISA kits. Proliferation was determined using alamarBlue™ (Alamar Biosciences, Sacramento, Calif.) after 96 hours.

| | IL & Cytokine Release Inhibition Assays ($IC_{50}$ μg/mL) | | | | | | | | | | | |
|---|---|---|---|---|---|---|---|---|---|---|---|---|
| | IL-1α | IL-1β | IL-2 | IL-4 | IL-5 | IL-6 | IL-10 | IL-12 | INFγ | TNFα | GMCSF | Pro-lif |
| FFW | 50 | 40 | 30 | 10 | 10 | 30 | <10 | 30 | 30 | 30 | 30 | 25 |
| PFFW | >100 | 38 | 16 | >100 | NT | >100 | >100 | >100 | >100 | <1.0 | NT | >100 |

(where NE = not effective;

NT = not tested;

FFW = Feverfew;

PFFW = substantially parthenolide-free feverfew,

IL = Interleukin (Cytokine);

IFN = interferon;

TNF = tissue necrosis factor;

GM-CSF = granulocyte macrophage stimulating factor).

Based on the foregoing, it can be seen that substantially parthenolide-free feverfew was able to modulate lymphocyte activation

EXAMPLE 3

Evaluation on RAW 264 Macrophage Cell Line

Raw 264 murine macrophage cells were stimulated 24 hours by 1 μg/ml of LPS and 10 U/ml of IFNγ in the presence or in the absence of the test products. Nitrites, the stable end product of nitric oxide, were assayed with the Griess reaction and PGE2 levels assessed by ELISA. Results are expressed as the percent inhibition of inflammatory mediator production compared to a stimulated control culture. Cell viability was checked with the MTT reduction test.

| RAW 264 Murine Marcophages Stimulate by LPS & IFNγ (% inhibition) | | |
|---|---|---|
| | $PGE_2$ | NO production |
| 0.001%-FFW | 33.0 | 16.1 |
| 0.01%-FFW | 78.0 | 58.4 |
| 0.1%-FFW | 98.0 | 99.9 |

FFW = feverfew, $PGE_2$ = prostaglandin $E_2$,

NO = nitric oxide

| RAW 264 Murine Marcophages Stimulate by LPS & IFNγ $IC_{50}$ μg/mL) | | | |
|---|---|---|---|
| Test material | Nitric Oxide | $PGE_2$ | $LD_{50}$ |
| FFW | 69 | 40 | 680 |
| FLAV | 89.0 | 4.0 | 250 |
| PFFW | 370 | 71 | 740 |

FFW = feverfew having 0.7% parthenolide,
PFFW = parthenolide-deprived feverfew having less than 0.1% parthenolide,
FLAV = feverfew containing 3% parthenolide and 26% flavoids (where the individual flavenoids are tanetin and 3,7,3'-trimethoxyquercetagetin comprising 7% and 22% of the flavenoid composition respectively),
$PGE_2$ = prostaglandin $E_2$,
NO = nitric oxide Based on the foregoing, it can be seen that PFFW was able to down-regulate an immune response.

EXAMPLE 4

Evaluation on Reconstituted Epidermis

The effect of substantially parthenolide-free feverfew on $PGE_2$ release from human epidermal equivalents was evaluated. Epidermal equivalents (EPI 200 HCF) were purchased form MatTeK Corporation. Upon receipt, epidermal equivalents were incubated for 24 hours at 37° C. in maintenance medium without hydrocortisone. Epidermal equivalents were pretreated for 2 hours with 50 μl of test product, washed and PMA (1 μg/ml) added to the culture medium. Equivalents were incubated for 24 hours at 37° C. with maintenance medium, culture supernatant collected and evaluated for $PGE_2$ and by ELISA. Viability was assessed with the MTT assay.

Thus, it can be seen that both z everfew extract and PFFW down-regulated the production of $PGE_2$.

EXAMPLE 5

Inhibition of Oxazolone Contact Hypersensitivity

The following experiments were carried out to test the effect of feverfew and substantially parthenolide-free feverfew in a contact hypersensitiveLy assay. In this assay, the compositions of the invention were evaluated against hydrocortisone, a steroid known to inhibit contact hypersensitivity. Albino male CD-1 mice, 7-9 weeks old, were induce on the shaved abdomen with 50 μL of 3% oxazolone in acetone/corn oil Day 0). On Day 5, a 20 μL volume of 2% oxazolone in acetone was appplied to the dorsal left ear of the mouse. Test compounds were applied to the left ear (20 μL) 1 hour after oxazolone challenge in a 70% ethanol/30% propylene glycol vehicle. The right ear was not treated. The mice were sacrificed by $CO_2$ inhalation 24 hours after the oxazolone challenge, the left and right ears were removed and a 7 mm biopsy was taken from each ear and weighed. The difference in biopsy weights between the right and left ear was calculated. Antiinflammatory effects of compounds are evident as an inhibition of the increase in ear weight.

| Oxazolone Contact Hypersensitivity Study (% Inhibition) | | | |
|---|---|---|---|
| Test Material | Study 1 | Study 2 | Study 3 |
| Hydrocortisone 0.1% | 96.9 | 87.6 | 91.0 |
| FFW 0.03% | 75.4 | NT | NT |
| FFW 0.1% | 89.9 | 64.5 | NT |
| FFW 0.3% | 91.9 | NT | NT |
| FFW 1.0% | 94.6 | NT | NT |
| PFFW 0.1% | NT | 54.7 | NT |
| Parthenolide 1.0% | NT | NT | 11 |

NT = Not tested

Thus, it can be seen that FFW and PFFW are effective in inhibiting reaction to oxazolone.

EXAMPLE 6

Mouse Ear Edema Inhibition Model

The following experiments were carried out to test the effect of feverfew and substantially parthenolide-free feverfew in a phorbol ester PITA) induced edema assay. In this assay, the compositions of the invention were evaluated against hydrocortisone and dexamethasone, steroids which are known to show efficacy in this model. Albino male CD-1 mice, 7-9 weeks old, were used. A 0.005% (w/v) TPA solution was made in acetone. A 20 μL volume of this TPA solution was applied to the dorsal left ear of the mouse. Test compounds were applied immediately to the left ear (20 μL) after TPA in a 70% ethanol/propylene glycol vehicle. The right ear was not treated. The mice were sacrificed by $CO_2$ inhalation (5.5 hours after TPA), the left and right ears were removed and a 7 mm biopsy was removed from each ear and weighed. The difference in biopsy weights between the right and left ear was calculated. Antiinflammatory effects of compounds are demonstrated by the inhibition of the increase in ear weight.

| Test Material | Study 1 | Study 2 |
|---|---|---|
| Hydrocortisone 0.1% | 96.9 | — |
| Dexamethasone 0.1% | — | 97.2 |
| FFW 0.1% | — | 14.7 |
| FFW 1% | 75.1 | — |
| PFFW 0.1% | — | 58.6 |

EXAMPLE 7

Inhibition of Arachidonic Acid Induced Ear Edema

In this in vivo model, feverfew's ability to reduce arachidonic acid induced edema was compared to the known cycloxygenase/lipoxgenase inhibitor tepoxalin. Albino male CD-1 mice, 7-9 weeks old, were used. A 20% (w/v) arachidonic acid (AA) solution was made in acetone. A 20 μl volume of the AA was applied to the dorsal left ear of the mouse. Test compounds (20 μl) were applied immediately to the left ear after AA in a 70% ethanol/30% propylene glycol vehicle. The right ear was not treated. The mice were sacrificed by $CO_2$ inhalation 1 hour after AA, the left and right ears were removed and a 7 mm biopsy was removed from each ear and weighed. The difference in biopsy weights between the right and left ear was calculated. Antiinflammatory effects of compounds are evident as an inhibition of the increase in ear weight.

| Inhibition of Arachidonic Acid Induced Ear Edema | |
|---|---|
| Test Material | % Inhibition |
| 0.1% Tepoxalin | 10.84 |
| 1.0% Tepoxalin | 42.38 |
| 2.0% Tepoxalin | 61.06 |
| 0.1% FFW | NE |
| 0.3% FFW | 23.86 |
| 1.0% FFW | 38.73 |

EXAMPLE 8

Prevention of Trauma Induced Inflammation Following Topical Application of Parthenolide Deprived Feverfew to Human Subjects Substantially parthenolide-free feverfew PFFW) was evaluated for its ability to prevent skin inflammation in a controlled human study involving 10 volunteers. In this study, parthenolide deprived everfew was tested at 0.1 and 1% and compared to its vehicle and hydrocortisone also at 0.1 and 1%. Test product was applied to the ventral side of the forearm twice daily for 2 consecutive days. Erythema was induced by 10 successive stratum corneum strippings. Chromameter measurements were made prior to stripping and at 0.5, 1, 1.5 and 2 hours posts tripping. The Colorimetric Erythema Index (CEI) was calculated for each time point. For the total 2 hour period, and compared to the vehicle, the following reductions in erythema were obtained;

| Test Material | Reduction of Erythema (%) |
|---|---|
| 0.1% Hydrocortisone | 10 |
| 1% Hydrocortisone | 19 |
| 0.1% PFFW | 22 |
| 1% PFFW | 35 |

These results demonstrate that substantially parthenolide-free feverfew is effective at preventing trauma induced inflammation in humans and has activity comparable to equal concentrations of hydrocortisone.

EXAMPLE 9

Prevention of UVB Induced Inflammation Following Topical Application of Parthenolide Deprived Feverfew to Human Subjects Parthenolide deprived feverfew (PFFW) was evaluated for its ability to prevent skin inflammation in a controlled human study involving 10 volunteers. In this study, PFFW was tested at 0.1 and 1% and compared to its vehicle and hydrocortisone also at 0.1 and 1%. Test product was applied to 5 different locations on the volar forearm twice daily for 2 consecutive days (2 mg/cm$^2$). The sites were exposed to 2MED UVB. Chromameter measurements were made prior to irradiation and at 18, 24, 42 and 48 hours post irradiation. The Colorimetric Erythema Index (CEI) was calculated for each time point. The following reductions in erythema were obtained:

| Test Material | Reduction of Erythema (%) |
|---|---|
| 0.1% Hydrocortisone | 2.5 |
| 1% Hydrocortisone | 5.7 |
| 0.1% PFFW | −3.5 |
| 1% PFFW | 24.9 |

These results demonstrate that parthenolide deprived feverfew is effective at preventing UV induced inflammation in humans.

EXAMPLE 10

Treatment of Trauma Induced Inflammation Following Topical Application of Substantially Parthenolide Free Feverfew to Human Subjects Substantially parthenolide-free feverfew (PFFW) was evaluated for its ability to prevent skin inflammation in a controlled human study involving 10 volunteers. In this study, PFFW was tested at 0.1 and 1% and compared to its vehicle and hydrocortisone also at 0.1 and 1%. Erythema was induced by 10 successive stratum corneum strippings. Test product was applied to the ventral side of the forearm for 2 hours, immediately after stripping. Chromameter measurements were made prior to stripping and at 0.5, 1, 1.5 and 2 hours post stripping. The Colorimetric Erythema Index (CEI) was calculated for each time point. For the total 2 hour period, and compared to the vehicle, the following reductions in erythema were obtained:

| Test Material | Reduction of Erythema (%) |
|---|---|
| 0.1% Hydrocortisone | −3 |
| 1% Hydrocortisone | 14 |
| 0.1% PFFW | −35 |
| 1% PFFW | 13 |

These results demonstrate that higher doses of substantially parthenolide-free feverfew are moderately effective at preventing trauma induced inflammation in humans and has activity comparable to equal concentrations of hydrocortisone.

EXAMPLE 11

Treatment of UVB Induced Inflammation Following Topical Application of Parthenolide Deprived Feverfew to Human Subjects Substantially parthenolide-free feverfew (PFFW) was evaluated for its ability to treat skin inflammation in a controlled human study involving 10 volunteers. In this study, PFFW was tested at 0.1 and 1% and compared to its vehicle and hydrocortisone also at 0.1 and 1%. Ten healthy volunteers were irradiated with 2MED UV light on five distinct spots of the volar forearms. Test product was applied (2 mg/cm$^2$) on the irradiated sites immediately after irradiation, and 5 and 8 hours later. Erythema scores were measured before irradiation and 1, 4, 7 and 24 hours later. The following reductions in erythema were obtained:

| Test Material | Reduction of Erythema (%) |
|---|---|
| 0.1% Hydrocortisone | 3.2 |
| 1% Hydrocortisone | 17.7 |
| 0.1% PFFW | 8.6 |
| 1% PFFW | 18.7 |

These results demonstrate that Parthenolide deprived feverfew is effective at treating UV induced inflammation in humans.

Examples 12 illustrates skin care composition according to the present invention. The compositions can be processed in conventional manner. They are suitable for cosmetic use. In particular, the compositions are suitable for applications to prevent and treat the inflammatory disorders and related conditions, such as but not limited to the conditions of contact dermatitis, edema, trauma induced inflammation, and UVB induced inflammation and thereof as well as for application to healthy skin to prevent or retard inflammation thereof.

EXAMPLE 12

This example illustrates an oil-in-water incorporating a composition of this invention.

| INGREDIENTS | % WT/WT |
|---|---|
| Glycerin, u.s.p. 99.5% | 2.00 |
| Allantoin | 0.55 |
| Dimethicone | 1.25 |
| Propylene glycol | 4.00 |
| Parthenolide-deprived feverfew | 1.00 |
| Hexylene glycol | 2.00 |
| Distearyldimonium chloride | 5.00 |
| Cetyl alcohol | 2.50 |
| Petrolatum, u.s.p. | 4.00 |
| Isopropyl palmitate | 3.00 |
| Pentylene glycol | 4.00 |
| Benzyl alcohol | 0.60 |
| Purified water, u.s.p. | 70.1 |

What is claimed is:

1. A topical composition comprising an effective amount of an extract of feverfew and a pharmaceutically acceptable excipient, wherein said extract is substantially free of α-unsaturated γ-lactone.

2. A topical composition of claim 1, wherein said extract contains less than 0.2% α-unsaturated γ-lactone.

3. A topical composition of claim 1, wherein said composition is in the form selected from the group consisting of a gel, cream, lotion, solution, powder, and ointment.

4. A topical composition of claim 2, wherein said composition is in the form selected from the group consisting of a gel, cream, lotion, solution, powder, and ointment.

5. A topical composition of claim 1, wherein said composition comprises between about 0.001% to about 10% by weight of said extract.

6. A topical composition of claim 4, wherein said composition comprises between about 0.001% to about 10% by weight of said extract.

7. A topical composition of claim 1, wherein said composition is comprised within a member selected from the group consisting of a bandage, a hydrocolloid dressing, a patch and a cloth wipe.

8. A topical composition of claim 6, wherein said composition is comprised within a member selected from the group consisting of a bandage, a hydrocolloid dressing, a patch and a cloth wipe.

9. A topical composition of claim 1, wherein said composition further comprises a retinoid.

10. A topical composition of claim 6, wherein said composition further comprises a retinoid.

11. A topical composition of claim 1, wherein said composition further comprises a salicylic acid and benzoyl peroxide.

12. A topical composition of claim 6, wherein said composition further comprises a compound selected from the group consisting of salicylic acid and benzoyl peroxide.

13. A topical composition of claim 1, wherein said composition further comprises a compound selected from the group consisting of a corticosteroid, an antifungal, an antibiotic, and an antiseptic.

14. A topical composition of claim 6, wherein said composition further comprises a compound selected from the group consisting of a corticosteroid, an antifungal, an antibiotic, and an antiseptic.

15. A topical composition of claim 1, wherein said composition further comprises an ingredient selected from the group consisting of a legume extract and oat protein.

16. A topical composition of claim 6, wherein said composition further comprises an ingredient selected from the group consisting of a legume extract and oat protein.

17. A topical composition of claim 1, wherein said composition further comprises a compound selected from the group consisting of a vitamin and a hydroxyl acid.

18. A topical composition of claim 6, wherein said composition further comprises a compound selected from the group consisting of a vitamin and a hydroxyl acid.

19. A topical composition of claim 1, wherein said composition further comprises dimethicone.

20. A topical composition of claim 6, wherein said composition further comprises dimethicone.

21. A topical composition of claim 1, wherein said composition further comprises a surface active agent.

22. A topical composition of claim 6, wherein said composition further comprises a surface active agent.

23. A topical composition of claim 1, wherein said composition further comprises a surface active agent.

24. A topical composition of claim 6, wherein said composition further comprises a surface active agent.

25. A topical composition of claim 1, wherein said composition further comprises an extract of green tea.

26. A topical composition of claim 6, wherein said composition further comprises an extract of green tea.

* * * * *